United States Patent [19]

Cavanak

[11] Patent Number: 5,759,997
[45] Date of Patent: *Jun. 2, 1998

[54] CYCLOSPORIN GALENIC FORMS

[75] Inventor: Thomas Cavanak, Biel-Benken, Switzerland

[73] Assignee: Novartis AG, Summit, N.J.

[*] Notice: The term of this patent shall not extend beyond the expiration date of Pat. No. 5,639,724.

[21] Appl. No.: 471,301

[22] Filed: Jun. 6, 1995

Related U.S. Application Data

[63] Continuation of Ser. No. 163,193, Dec. 6, 1993, Pat. No. 5,639,724, which is a continuation of Ser. No. 940,119, Sep. 3, 1992, abandoned, which is a continuation of Ser. No. 822,375, Jan. 17, 1992, abandoned, which is a continuation of Ser. No. 481,082, Feb. 16, 1990, abandoned, which is a continuation-in-part of Ser. No. 462,373, Jan. 9, 1990, abandoned, which is a continuation of Ser. No. 373,736, Jun. 29, 1989, abandoned, which is a continuation of Ser. No. 193,986, May 13, 1988, abandoned, which is a continuation of Ser. No. 901,356, Aug. 28, 1986, abandoned, which is a continuation of Ser. No. 633,808, Jul. 24, 1984, abandoned.

[30] Foreign Application Priority Data

Feb. 20, 1989 [GB] United Kingdom ............... 8903804

[51] Int. Cl.$^6$ .......................... A61K 38/13; A61K 47/14
[52] U.S. Cl. ............................ 514/11; 514/785; 514/786
[58] Field of Search ................................ 530/317, 321; 514/9, 11, 785, 786, 885, 974

[56] References Cited

U.S. PATENT DOCUMENTS

| 3,288,824 | 11/1966 | Mahler et al. ............... 554/168 |
| --- | --- | --- |
| 4,388,307 | 6/1983 | Cavanak ........................ 514/2 |
| 4,390,548 | 6/1983 | Yamato et al. ................ 564/98 |
| 4,990,337 | 2/1991 | Kurihara et al. ............... 514/15 |
| 5,338,761 | 8/1994 | Nakajima et al. ............ 514/772 |
| 5,639,724 | 6/1997 | Cavanak ........................ 514/11 |

FOREIGN PATENT DOCUMENTS

| 895724 | 7/1983 | Belgium . |
| --- | --- | --- |
| 0170623 | 2/1986 | European Pat. Off. ....... A61K 37/02 |
| 2461/78 | 6/1983 | Switzerland . |
| 8634/78 | 6/1983 | Switzerland . |
| 641356 | 2/1984 | Switzerland . |
| 2098865 | 12/1982 | United Kingdom . |
| 2120935 | 12/1983 | United Kingdom . |
| 2211848 | 7/1989 | United Kingdom ........... A61K 37/02 |

OTHER PUBLICATIONS

Cavanak, T., et al., Formulation of Dosage Forms, Prog. Allergy, vol. 38, pp. 65–72 (1986).
Reymond, J., et al., In Vitro Model for Ciclosporin Intestinal Absorption in Lipid Vehicles, Pharmaceutical Research, vol. 5, No. 10, pp. 673–676 (1988).
Reymond, J., In Vitro In Vivo Model For The Absorption of Cyclosporin A Dissertation, University of Basel (1986).
Miglyol–Neutral Oils, Dynamit Nobel Chemicals (1975).
Chemical Abstracts, 89: 117874s (Jun. 8, 1978).
Chemical Abstracts, 89: 117875t (Jun. 8, 1978).
Derwent Abstracts, 84–069426/12 (Feb. 19, 1984).
Chemical Abstracts 92:64765k (1980).

*Primary Examiner*—Jeffrey E. Russel
*Attorney, Agent, or Firm*—Marla J. Mathias

[57] ABSTRACT

Pharmaceutical compositions comprising a cyclosporin as active ingredient, a fatty acid triglyceride, a glycerol fatty acid partial ester or propylene glycol or sorbitol complete or partial ester, preferably, and a tenside having an HLB of at least 10.

12 Claims, No Drawings

CYCLOSPORIN GALENIC FORMS

This is a continuation of application Ser. No. 08/163,193, filed Dec. 6, 1993, now U.S. Pat. No. 5,639,724, which in turn is a continuation of application Ser. No. 07/940,119, filed Sep. 3, 1992, now abandoned, which in turn is a continuation of application Ser. No. 07/822,375, filed Jan. 17, 1992, now abandoned, which in turn is a continuation of application Ser. No. 07/481,082, filed Feb. 16, 1990, now abandoned, which in turn is a continuation-in-part of application Ser. No. 07/462,373, filed Jan. 9, 1990, now abandoned, which in turn is a continuation of application Ser. No. 07/373,736, filed Jun. 29, 1989, now abandoned, which in turn is a continuation of application Ser. No. 07/193,986, filed May 13, 1988, now abandoned, which in turn is a continuation of application Ser. No. 06/901,356, filed Aug. 28, 1986, now abandoned, which in turn is a continuation of application Ser. No. 06/633,808, filed Jul. 24, 1984, now abandoned.

The present invention relates to novel galenic formulations, in particular novel pharmaceutical compositions as well as novel oral dosage forms comprising a cyclosporin as active ingredient.

The cyclosporins comprise a class of structurally distinctive, cyclic, poly-N-methylated undercapeptides, commonly possessing pharmacological, in particular immunosuppressive, anti-inflammatory and/or anti-parasitic (in particular anti-protozoal, e.g. anti-malarial) activity. The first of the cyclosporins to be isolated was the naturally occurring fungal metabolite Ciclosporin or Cyclosporine, also known as cyclosporin A and commercially available under the Registered Trade Mark SANDIMMUN® or SANDIMMUNE®. Ciclosporin is the cyclosporin of formula A.

```
┌─ MeBmt-αAbu-Sar-MeLeu-Val-MeLeu-Ala-(D)Ala-MeLeu-MeLeu-MeVal ─┐    (A)
│      1    2   3    4    5    6    7    8     9     10    11   │
└────────────────────────────────────────────────────────────────┘
``` wherein -MeBmt- represents the N-methyl-(4R)-4-but-2E-en-1-yl-4-methyl-(L)threonyl residue of formula B

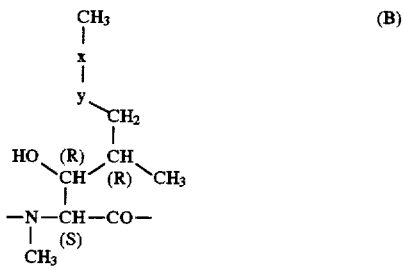

(B)

in which -x-y- is —CH=CH— (trans).

As the parent of the class, Ciclosporin has so far received the most attention. The primary area of clinical investigation for Ciclosporin has been as an immunosuppressive agent, in particular in relation to its application to recipients of organ transplants, e.g. heart, lung, combined heart-lung, liver, kidney, pancreatic, bone-marrow, skin and corneal transplants and, in particular, allogenic organ transplants. In this field Ciclosporin has achieved a remarkable success and reputation.

At the same time, applicability of Ciclosporin to various autoimmune diseases and to inflammatory conditions, in particular inflammatory conditions with an aetiology including an autoimmune component such as arthritis (for example rheumatoid arthritis, arthritis chronica progrediente and arthritis deformans) and rheumatic diseases, has been intensive and reports and results in vitro, in animal models and in clinical trials are wide-spread in the literature. Specific auto-immune diseases for which Ciclosporin therapy has been proposed or applied include, autoimmune hematological disorder (including e.g. hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine opthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Further areas of investigation have been potential applicability as an anti-parasitic, in particular anti-protozoal agent, with possible uses suggested including treatment of malaria, coccidiomycosis and schistosomiasis and, yet more recently, use in cancer therapy, e.g. as an agent for reversing or abrogating resistance to other anti-neoplastic or cytostatic therapy.

Since the original discovery of ciclosporin, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes, for example, the naturally occurring cyclosporins A through Z [c.f. Traber et al. 1, Helv. Chim. Acta. 60, 1247–1255 (1977); Traber et al. 2, Helv. Chim. Acta. 65 no. 162, 1655–1667 (1982); Kobel et al., Europ. J. Applied Microbiology and Biotechnology 14, 273–240 (1982); and von Wartburg et al., Progress in Allergy, 38, 28–45 (1986)], as well as various non-natural cyclosporin derivatives and artificial or synthetic cyclosporins including the so called dihydro-cyclosporins [in which the moiety -x-y- of the -MeBmt- residue (Formula B above) is saturated to give -x-y-=—CH$_2$—CH$_2$—]; derivatised cyclosporins (e.g. in which a further substituent is introduced at the α-carbon atom of the sarcosyl residue at the 3-position of the cyclosporin molecule); cyclosporins in which the -MeBmt- residue is present in isomeric form (e.g. in which the configuration across positions 6' and 7' of the -MeBmt-residue is cis rather than trans); and cyclosporins wherein variant amino acids are incorporated at specific positions within the peptide sequence, employing e.g. the total synthetic method for the production of cyclosporins developed by R. Wenger—see e.g. Traber 1, Traber 2 and Kobel loc. cit.; U.S. Pat. Nos. 4,108,985, 4,210,581 and 4,220,641; European Patent Publication Nos. 0 034 567, 0 056 782 and 0 296 122; International Patent Publication No. WO 86/02080; Wenger 1, Transp. Proc. 15, Suppl. 1:2230 (1983); Wenger 2, Angew. Chem. Int. Ed., 24, 77 (1985); and Wenger 3, Progress in the Chemistry of Organic Natural Products 50, 123 (1986).

The class comprised by the cyclosporins thus now includes, for example, [Thr]$^2$-, [Val]$^2$-, [Nva]$^2$- and [Nva]$^2$-[Nva]$^5$-Ciclosporin (also known as cyclosporins C,D, G and M respectively), [3'-0-acyl-MeBmt]$^1$-Ciclosporin (also known as cyclosporin A acetate), [Dihydro-MeBmt]$^1$-[Val]$^2$-Ciclosporin (also known as dihydro-cyclosporin D), [3'-Desoxy-3'-oxo-MeBmt]$^1$[Val]$^2$- and -[Nva]$^2$-Ciclosporin, [(D)Fluoromethyl-Sar]$^3$-Ciclosporin, [(D)Ser]$^8$-Ciclosporin, [MeIle]$^{11}$-Ciclosporin, [(D)MeVal]$^{11}$-Ciclosporin (also known as cyclosporin H), [MeAla]$^6$-Ciclosporin, [(D)Pro]$^3$-Ciclosporin and so on.

[In accordance with now conventional nomenclature for cyclosporins, these are defined by reference to the structure of Ciclosporin (i.e. Cyclosporin A). This is done by first indicating the amino acid residues present which differ from those present in Ciclosporin (e.g. "[(D)Pro]$^3$" to indicate that the cyclosporin in question has a -(D)Pro- rather than -Sar-residue at the 3-position) and then applying the term "Ciclosporin" to characterise remaining residues which are identical to those present in Ciclosporin. Individual residues are numbered starting with the residue -MeBmt-, -dihydro-MeBmt- or its equivalent in position 1.]

Very many of these further cyclosporins exhibit comparable pharmaceutical utility to Ciclosporin or more specific utility, for example activity particularly in reversing tumor resistance to cytostatic therapy, and proposals for their application as therapeutic agents abound in the literature.

Despite the major contribution which Ciclosporin has made, in particular to the areas of organ transplant and the therapy of autoimmune diseases, difficulties encountered in providing more effective and convenient means of administration (e.g. galenic formulations, for example oral dosage forms, which are both convenient for the patient as well as providing appropriate bio-availability and allowing dosaging at an appropriate and controlled dosage rate) as well as the reported occurrence of undesirable side reactions, in particular nephrotoxic reaction, have been obvious serious impediments to its wider use or application.

The cyclosporins are characteristically highly hydrophobic and readily precipitate in the presence of even very minor amounts of water, e.g. on contact with the body (e.g. stomach) fluids. It is accordingly extremely difficult to provide, e.g. oral formulations which are acceptable to the patient in terms of form and taste, which are stable on storage and which can be administered on a regular basis to provide suitable and controllable patient dosaging.

Proposed liquid formulations, e.g. for oral administration of cyclosporins, have hitherto been based on the use of oils in conjunction with solvent systems comprising, e.g. ethanol and LABRAFIL and equivalent excipients as carrier media. Thus the commercially available Ciclosporin drink-solution employs ethanol and olive oil or corn-oil as carrier medium in conjunction with a Labrafil as co-solvent—see e.g. U.S. Pat. No. 4,388,307. Use of the drink-solution and similar compositions as proposed in the art is however accompanied by a variety of difficulties.

First the palatability of the known oil based systems has proved problematic. The taste of the known drink-solution is, in particualr, unpleasant and admixture with an appropriate flavoured drink, for example chocolate drink preparation, at high dilution immediately prior to ingestion has generally been practiced in order to make regular therapy at all acceptable. Adoption of oil based systems hitherto has also required the use of high ethanol concentrations to maintain solubility. Use of ethanol is in itself inherently undesirable, in particular where administration to children is foreseen. In addition, evaporation of the ethanol, e.g. from encapsulated forms (adopted, in large part, to meet problems of palatibility as discussed above), or other forms (e.g. when opened) results in development of a precipitate. Where such compositions are presented in e.g. soft gelatin encapsulated form, this particular difficulty necessitates packaging of the encapsulated product in an air-tight compartment, for example an air-tight blister or aluminium-foil blister package or container. This in turn renders the product both bulky and more expensive to produce. The storage characteristics of such formulations are thus far from ideal.

Use of such dosage forms is also characterised by extreme variation in required patient dosaging. In order to achieve effective immunosuppressive therapy, cyclosporin blood or blood serum levels have to be maintained within in a specified range. This range in turn can vary, depending on the particular condition being treated, e.g. whether therapy is to prevent transplant rejection or for the control of an autoimmune disease or condition, and on whether or not alternative immunosuppressive therapy is employed concomitantly with cyclosporin therapy. Experience shows however that, e.g. employing the available Ciclosporin drink solution, daily dosages needed to achieve required blood serum levels vary considerably from individual to individual and even for a single individual at different times. For this reason it is necessary to monitor blood/blood-serum levels of patients receiving Ciclosporin therapy at regular and frequent intervals in order that the daily dosage taken may be adjusted to maintain blood/blood-serum levels within the required range. Monitoring of blood/blood-serum levels, which is generally performed by RIA or equivalent immunoassay technique, e.g. employing monoclonal antibody based technology, has to be carried out for each patient receiving Ciclosporin therapy on a regular basis. This is inevitably time consuming and inconvenient and adds substantially to the overall cost of therapy.

It is also the case that blood/blood-serum cyclosporin levels achieved using available dosage systems exhibit extreme variation between peak and trough levels. That is, for each patient, effective cyclosporin levels in the blood vary widely between administration of individual dosages. This variation in patient response has been found to be attributable to a significant extent to variation in the availability of naturally occurring surfactant components, e.g. bile acids and salts, within the gastro-intestinal tract of the subject treated. For galenic formulations for cyclosporins hitherto known in the art, the presence of such natural surfactants in sufficient quantity is required if satisfactory resorption is to be achieved. However the availability of such surfactants in the gastro-intestinal tract inevitably varies from subject to subject and in individual subjects with time.

Apart from the unsatisfactory nature of such inconsistancy in therapy, this also means that individual patients must be monitored on each occasion within a relatively narrow time-window, to ensure, e.g. that a peak level is not inadvertantly recorded as a high response to dosage.

Beyond all these very evident practical difficulties lies the occurrence of undesirable side reactions already alluded to, observed employing available oral dosage forms.

Several proposals to meet these various problems have been suggested in the art, including both solid and liquid oral dosage forms. An overriding difficulty has however remained the inherent insolubility of the cyclosporins, e.g. Ciclosporin, in aqueous media and hence provision of a dosage form which can contain cyclosporins in sufficiently high concentration to permit convenient use and yet meet the required criteria in terms of bioavailability, e.g. enabling effective resorption from the stomach or gut lumen and achievement of consistent and appropriately high blood/blood-serum levels.

As already noted, current commercial oral dosage forms for Ciclosporin are disclosed and claimed, e.g. in U.S. Pat. No. 4,388,307. The early phase of this development is reflected in Swiss patent application no. 8634/78-8 which serves as a priority document to this patent. This application is directed to galenic formulations comprising Ciclosporin as the active ingredient together with a carrier medium comprising any one or more of the following components:

i) sesame oil;

ii) a non-ionic tenside, e.g. TWEEN 80, CREMOPHORE EL. 40 or 60 or lecithins;

iii) a trans-esterified non-ionic triglyceride, e.g. LABRAFIL;

iv) mixtures of a lecithin (e.g. EPIKURON), ingredients (iii) and ethyloleate;

v) neutral oils, e.g. saturated $C_{8-12}$triglycerides such as MIGLYOL 812; and vi) mono- and/or di-glycerides such as glycerol monooleate, glycerol monostearate and glycerol distearate.

In the text and examples: (i) is described for use alone, for oral or parenteral administration; (ii) are described for use in combination with ethanol for oral or parenteral administration and in combination with components (v) for parenteral application; (iii) are described for use alone and in conjunction with a vegetable oil and, additionally, ethanol for oral or parenteral administration; (iv) is described in terms of the defined combination with possible further additives, for example conserving agents, for oral administration; (v) are described for use in combination with solvents such as ethanol, benzoic acid benzyl ester, 1,2-butyleneglycol-1-methyl ether and components (iii) (LABRAFIL) as well as in combination with components (ii) as set forth above, in particular for parenteral administration; and (vi) are described for use alone or in combination with thickening agents such as aerosil or cellulose for oral administration in encapsulated or pelleted form. No specific proposal is made for the combination of components (vi) [mono-/di-glycerides] with any other component (i) to (v), or vice versa.

In the patent application which matured as U.S. Pat. No. 4,388,307, the focus of development set out in the above Swiss application is concentrated on compositions comprising cyclosporins as active ingredient, together with a carrier medium comprising one or more of components (iii) [LABRAFIL etc.], (v) [neutral oils] and (vi) [mono-/di-glycerides, in particular stearic or oleic mono/di-glycerides, especially glycerol monooleate]. In relation to oral dosage forms, use of co-solvents, ethanol and vegetable oils such as olive oil and corn oil, is preferred. Components (v) are specifically indicated as preferred in relation to parenteral, dosage forms. Components (vi) are proposed for use with lecithins, optionally together with components (iii) in orally administered aqueous or aqueous/ethanolic emulsions.

Belgian Patent no. 895 724, which relates primarily to the use of [dihydro-MeBmt]$^1$-[Val]$^2$-Ciclosporin (or dihydro-cyclosporin D) in the treatment of multiple sclerosis, also describes two oral formulations suitable for the administration of this particular compound. Both of these are based on the commercial Ciclosporin (SANDIMMUN) drink-solution, with adaptation to suit the particular cyclosporin active ingredient. The first comprises 5–10% [Dihydro-MeBmt]$^1$-[Val]$^2$-Ciclosporin, 10–12% ethanol, 30–40% MAISINE, ca. 4% CREMOPHORE and 51–30% LABRAFIL (i.e. to 100%). This corresponds to the composition of the SANDIMMUN drink-solution, but with the replacement of the natural vegetable oil component with MAISINE and introduction of a minor pecentage of the tenside CREMPHORE. MAISINE is a trans-esterification product of corn oil with glycerol, the more precise composition of which is described hereinafter. It comprises corn oil derived triglycerides and mono-/di-glycerides in the ratio ca. 1:8 p.p.w (tri-:mono-/di-glycerides). The ratio of cyclosporin: tenside in the disclosed composition is ca. 1:0.4-0.8, and the ratio of cyclosporin: triglycerides: mono-/di-glycerides is ca. 1:0.4-0.9:2.6-7.1. No proposal is made for possible increase in the tenside component nor for any means of avoiding the use of LABRAFIL or ethanol components as co-solvents.

The second disclosed composition comprises: 15–25% [Dihydro-MeBmt]$^1$-[Val]$^2$-Ciclosporin, 2–5% ethanol, 40–60% MAISINE and 10–40% IMWITOR 742, a coconut oil mono-glyceride product comprising >45% monoglycerides with additional di- and tri-glyceride components. Again, the use of ethanol is not avoided and no proposal is made for incorporation of any tenside component.

Australian patent application no. discloses the use of tensides belonging to the group comprising polyethoxylated castor oils, polyethoxylated hydrogenated castor oils and polyethoxylated fatty acids derived from castor oil or hydrogenated castor oil, such as CREMOPHOR, MYRJ, and NIKKOL HCO-60 as solubilizers for the incorporation of difficultly soluble pharmaceutical agents into controlled release systems, such as hydrophilic gel systems. Difficultly soluble pharmaceuticals recited include Ciclosporine, though no example of the application of the system to cyclosporins is given. Nor is there any teaching for the use of the recited solubilizers/tensides in conjunction with simple fatty acid mono-, di- or tri-glycerides.

In accordance with the present invention, it has now surprisingly been found that pharmaceutical compositions comprising cyclosporins, in particular Ciclosporin, as active ingredient, which meet or substantially reduce difficulties in dosaging and patient acceptability hitherto encountered in the art, e.g. as discussed above, can be achieved by the use of carrier systems comprising fatty acid tri-glycerides and mono-/di-glycerides, suitably in combination or conjunction with a hydrophilic tenside. In particular, it has been found that, employing the defined carrier systems, it is possible to obtain oil-based compositions, which are not aqueous emulsions, and which do not require the presence of additional solvents, co-solvents or solubilizers, for example ethanol or LABRAFIL or the like, and which exhibit high stability as well as improved bioavailability characteristics as compared with known cyclosporin/fatty acid triglyceride/solvent/co-solvent systems, for example, the known SANDIMMUN® drink-solution. In a specific aspect the present invention provides for oil-based pharmaceutical compositions, in particular oil-based pharmaceutical compositions other than aqueous emulsions, which are free or substantially free of ethanol.

In particular, it has been found that compositions in accordance with the present invention enable effective cyclosporin dosaging with concomitant enhancement of resorption/bioavailability levels, and/or reduced variability in resorption/bioavailability levels, achieved both for individual patients receiving cyclosporin therapy as well as between individuals. In particular it has surprisingly been found that the compositions of the invention enable resorption of cyclosporins in a manner that is independent, or of substantially reduced dependency, upon the relative availability of natural surfactant materials, e.g. bile acids or salts, in the gastro-intestinal tract of the subject treated. By application of the teachings of the present invention, cyclosporin dosage forms are obtained providing reduced variability in achieved cyclosporin blood/blood serum levels between dosages as well as between individuals. The invention thus enables reduction of cyclosporin dosage levels required to achieve effective therapy. In addition, it permits closer standardisation as well as optimisation of on-going daily dosage requirements for individual subjects receiving cyclosporin therapy as well as for groups of patients undergoing equivalent therapy.

By closer standardisation of individual patient dosaging rate and blood/blood-serum level response, as well as dosaging and response parameters for patient groups, monitoring requirements may be reduced, thus substantially reducing the cost of therapy.

By reduction of required cyclosporin dosaging/standardisation of achieved bio-availability characteristics, the present invention also provides a means which may permit reduction in the occurrence of undesirable side-effects, in particular nephrotoxic reaction, in patients undergoing cyclosporin therapy.

In addition, the compositions of the invention exhibit improved stability on storage as compared with compositions based on the use of ethanol or equivalent alkanols and are, in particular, better adapted, e.g. for presentation in capsule, e.g. hard or soft gelatin capsule, form. Compositions in accordance with the findings of the present invention which a or substantially free of ethanol have the particular advantage of eliminating or substantially reducing packaging difficulties, for example as hereinbefore discussed, e.g. in relation to the packaging of soft gelatin encapsulated forms.

In accordance with the present invention there is provided, in its broadest aspect:

A. A pharmaceutical composition comprising:
 a) a cyclosporin as active ingredient in a carrier medium comprising
 b) a fatty acid triglyceride and
 c) a glycerol fatty acid partial ester or propylene glycol (e.g. 1,2-propylene glycol) or sorbitol complete or partial ester.

The term "pharmaceutical composition" as used throughout the present specification and accompanying claims is to be understood as defining compositions of which the individual components or ingredients are themselves pharmaceutically acceptable, e.g. where oral administration is foreseen, acceptable for oral use or, where topical administration is foreseen, topically acceptable.

Component (a) in the compositions of the invention may be any therapeutically applicable cyclosporin, e.g. as hereinbefore indicated. The preferred component (a) in the compositions of the invention is Ciclosporin. A further preferred component (a) in the compositions of the invention is [Nva]$^2$-Ciclosporin, also known as cyclosporin G.

Components (b) and (c) in the compositions of the invention may comprise or consist or consist essentially of the individual components (b) and (c) of a single ingredient, e.g. single material or product. Suitable products of this type include, in particular, transesterification products of vegetable oils with glycerol, propylene glycol (e.g. 1,2-propylene glycol) or sorbitol.

Accordingly, in one particular series of embodiments the present invention provides:

$B^1$ A pharmaceutical composition comprising:
 a) a cyclosporin as active ingredient in a carrier medium comprising
 b+c) a transesterification product of a vegetable oil with glycerol, propylene glycol or sorbitol;

$B^2$ A pharmaceutical composition comprising:
 a) cyclosporin as active ingredient in a carrier medium comprising
 b+c) a transesterification product of a vegetable oil with glycerol or sorbitol; and $B^3$ A pharmaceutical composition comprising:
 a) a cyclosporin as active ingredient in a carrier medium comprising
 b+c) a transesterification product of a natural vegetable oil and glycerol or sorbitol.

Ingredients (b+c) for use in compositions of the invention as defined under $B^1$ to $B^3$ above include trans-esterification products of any appropriate natural (e.g. non-hydrogenated) or hydrogenated vegetable oil. Suitably they are, as specifically in the case of definition $B^3$, trans-esterification products of natural vegetable oils, for example, almond oil, ground-nut oil, olive oil, palm oil or, preferably, corn oil.

Such trans-esterification products [ingredients (b+c)] are generally obtained by heating of the vegetable oil, e.g. corn oil, with glycerol, propylene glycol or sorbitol [e.g. glycerol or sorbitol], at high temperature under an inert atmosphere with continuous agitation, e.g. in a stainless steel reactor, to effect trans-esterification, e.g. glycerolysis, glycolysis or sorbitolysis. Ingredients (b+c) thus comprise mixtures of mono-, di- and tri-glycerides (i.e. glycerol mono-, di- and tri-esters) with generally minor amounts of free glycerol.

Where ingredients (b+c) for use in the invention are obtained by trans-esterification of a vegetable oil with sorbitol they will also contain free sorbitol as well as sorbitol mono-, di-, tri- and tetra-esters.

Where ingredients (b+c) for use in the invention are obtained by trans-esterification of a vegetable oil with propylene glycol they will also contain free propylene glycol (e.g. 1,2-propylene glycol) as well as propylene glycol mono- and di-esters.

In general free sorbitol/free propylene glycol will be present in relatively minor amounts, the recited mono-, di-, as well as tri- and tetra-esters when sorbitol is employed, in relatively substantial amounts.

The amount of triglyceride present in ingredients (b+c) for use in the invention will preferably be substantial, e.g. in excess of 5%, suitably from 7.5 to 12% by weight based on the total weight of the individual components (b) and (c) in said ingredient.

The amount of free glycerol plus any free propylene glycol or sorbitol present in ingredients (b+c) for use in the invention is preferably less than 10%, more preferably less than 5%, most preferably 1 to 2% or less based on the total weight of said ingredient. The amount of mono-glyceride present in ingredients (b+c) for use in the invention is preferably ca. 25 to 50%, more preferably ca. 30 to 45%, by weight based on the total weight of said ingredient.

When (b+c) is a trans-esterification product of a vegetable oil, e.g. corn oil, and glycerol, the amount of free glycerol present in said product is preferably less than 10%, more preferably less than 5%, most preferably less than ca. 4% by weight. The amount of mono-glyceride present is preferably about 30 or 35 to 50% by weight, more preferably about 35 or 40 to 45% by weight. The amount of di-glyceride present is preferably less than about 60%, suitably less than 40%, by weight. The amount of tri-glyceride present is preferably up to about 10% by weight, e.g. ca. 7.5 to 12 or 14% by weight (all percentages being based on the total weight of said product). The ratio of the components (b):(c) in the defined trans-esterification products is thus suitably of the order of ca. 1:8 to ca. 1:9 p.p.w.

When (b+c) is a trans-esterification product of a vegetable oil, e.g. corn oil, and sorbitol, the amount of free glycerol plus free sorbitol present in said product is preferably less than 5% by weight, more preferably ca. 1 to 2% by weight. The amount of mono-glyceride present is preferably ca. 30 to 40% by weight, more preferably ca. 35% by weight (all percentages being based on the total weight of said product).

Particularly suitable trans-esterification products [ingredients (b+c)] for use in accordance with the present invention are trans-esterification products of corn oil and glycerol, for example as commercially available under the trade name MAISINE. Such products are comprised predominantly of linoleic and oleic acid mono-, di- and tri-glycerides together with minor amounts of palmitic and stearic acid mono-, di- and tri-glycerides (corn oil itself being comprised of ca. 56% by weight linoleic acid, 30% oleic acid, ca. 10% palmitic and ca. 3% stearic acid constituents). Physical characteristics for MAISINE [available from the company Etablissements Gattefossé, of 36, Chemin de Genas, P.O.Box 603, 69804 Saint-Priest, Cedex (France)] are: approximate composition free glycerol—10% max. (typically 3.9–4.9% or, in more recent batches, ca. 0.2%)

monoglycerides—ca. 40% (typically 41–44.1% or, in more recent batches, ca. 38%)

diglycerides—ca. 40% (or, in more recent batches, ca. 46%)

triglycerides—ca. 10% (or, in more recent batches, ca. 12%)

free oleic acid content—ca. 1%

Further physical characteristics for MAISINE are: acid value=max. ca. 2, iodine no.=ca. 85–105, saponification no.=ca. 150–175, mineral acid content=0.

The fatty acid content for MAISINE, is typically: palmitic acid-ca. 11%; stearic acid-ca. 2.5%; oleic acid-ca. 29%; linoleic acid-ca. 56%; others-ca. 1.5%.

Further trans-esterification products [ingredients (b+c)] suitable for use in accordance with the present invention are trans-esterification products of corn oil and sorbitol, for example as commercially available under the trade name SORBITO GLYCERIDE from the company Etablissements Gattefossé, for example SORBITO GLYCERIDE WL 713, which has the following approximate composition:

Product: trans-esterification product of ca. 2 Mol corn oil and ca. 1 Mol sorbitol:

Approximate composition

| free glycerol | } - ca. 1 to 2% |
|---|---|
| free sorbital monoglycerides | - ca. 35% | plus: di- and tri-glycerides and sorbitol mono-, di-, tri- and tetra-esters.

Color (Echelle Garner)=<8. Highly soluble in ethanol and chloroform/slightly soluble in ethyl-ether/insoluble in H₂O. Acid no.=<1; saponification no.=ca. 160–185; iodine no.=ca. 110–140.

The carrier medium of compositions in accordance with $B^1$ to $B^3$ above may comprise (b+c) alone or together with one or more additional excipients, additives or other ingredients as known in the art, for example diluents, solvents, stabilizing agents, tensides, sweetening agents, preserving agents and/or flavouring agents.

Where ingredient (b+c) is semi-solid or of high viscosity e.g. as in the case of MAISINE, the addition of a diluent or solvent to reduce viscosity will be especially advantageous, in particular to improve handlability of the composition, for example to facilitate filling into containers, particularly where these are of small diameter as in the case of ampoules, capsules and the like. Accordingly in a further embodiment the present invention also provides:

$B^4$ A pharmaceutical composition as defined under any one of $B^1$ to $B^3$ above additionally comprising:
  d) a solvent or diluent miscible with (b+c) and reducing, or capable of reducing, the viscosity of (b+c).

When present, component (d) suitably comprises a trans-esterification product of a natural vegetable oil triglyceride and a polyalkylene polyol. Such trans-esterification products are known from the art and may be obtained e.g. in accordance with the general procedures described in U.S. Pat. No. 3,288,824. They include transesterification products of various natural (e.g. non-hydrogenated) vegetable oils for example, maize oil, kernel oil, almond oil, ground nut oil, olive oil and palm oil and mixtures thereof with polyethylene glycols, in particular polyethylene glycols having an average molecular weight of from 200 to 800. Preferred components (d) are trans-esterification products obtained from maize oil. Further preferred as (d) are products obtained by trans-esterification product of the class defined are commercially available from Etablissement Gattefossé, Boulogne sur Seine, France under the trade name LABRAFIL [see Fiedler, loc. cit., page 539]. A preferred component (d) is the product LABRAFIL M 2125 CS, a polyoxyethylated, maize oil having an acid no.=ca. 2, a saponification no.=ca. 155–175 and an iodine no.=ca. 90–100.

Use of LABRAFIL as component (d) is especially indicated where the compositions of the invention are to be filled into ampoules or the like for use as the base for a "drink solution" e.g. as hereinafter described.

Further, especially advantageous components (d) are (additional) components (c) as defined under A above, in particular mono- and di-glycerides, e.g. comprising an esterification product of caprylic and capric acid with glycerol. Use of such components (c) as (d) provides compositions in accordance with the invention conforming with the invention as hereinafter defined under C.

Examples of suitable components (c) for use as (d) include any of those described under (c.1) to (c.6) below. Especially preferred components (c) for use as (d) comprise products obtained by esterification of from about 50 to 75, e.g. about 60, parts by weight of capric acid with glycerol, and comprising, or consisting mainly or essentially of caprylic/capric acid mono- and di-glycerides. Especially preferred products of this class are those available under the trade name IMWITOR as described under (c.1) below, in particular the product IMWITOR 742.

A further possible, though less preferred, component (d) is ethanol, e.g. absolute ethanol.

In addition it has also been found that the bio-availability of the compositions in accordance with $B^1$ to $B^3$ above may be further increased if they additionally comprise an emulsifying agent. Accordingly, in yet a further embodiment, the present invention additionally provides:

$B^5$ A pharmaceutical composition as defined under any one of $B^1$ to $B^4$ above additionally comprising:
  e) an emulsifying agent.

Components (e) may or may not be directly miscible (e.g. capable of forming a solution, suspension or the like) with other components present in the compositions defined, e.g. components (a) and (b+c). Where components (e) are non-miscible, the compositions of the invention will be bi-phasic, i.e. comprise at least a double-system e.g. with components (a) and (b+c) and, optionally, (d) comprised in a first layer or phase of the composition and component (e) comprised in a second, separate layer or phase above or below the said first layer or phase (depending on the relative specific gravity of the two layers or phases). Such bi-phasic compositions are also to be understood as being within the purview of the present invention. Where the compositions of the invention are bi-phasic, separate phases may be com-mingled prior to administration, e.g. by shaking, stirring or other agitation, or may be contained together within a single unit dosage form, e.g. capsule or the like, so as to permit concommitant administration and release within the gastro-intestinal tract.

Component (e), when present, preferably comprises a tenside having a hydrophilic-lipophilic balance (HLB) of at least 10. Examples of suitable components (e) include any of those described under (e'.1) to (e'.8) below, in particular under (e'.1), most especially those known and commercially available under the trade name CREMOPHORE, for example CREMOPHORE RH40.

In the compositions of the invention in accordance with $B^1$ to $B^5$ above, (a) is suitably present in an amount of from about 2.0 to about 20%, preferably from about 5 to 15%, most preferably about 10% by weight, based on the total weight of the composition. Accordingly, when (b+c) is present alone, this will generally be present in an amount of from about 80 to about 98%, preferably from about 75 to about 95%, most preferably about 90% based on the total weight of the composition.

When (d) is present and is a trans-esterification product of a natural vegetable oil triglyceride and a polyalkylene polyol (for example a LABRAFIL), (d) is suitably present in an amount of up to about 50%, preferably from about 20 to about 40%, most preferably about 30%, based on the total weight of the composition.

When (d) is present and is an esterification product of caprylic and caproic acid with glycerol (for example an IMWITOR), (d) is suitably present in an amount of up to 40%, preferably in an amount of from about 2 to about 40%, most preferably in an amount of from about 2 to 20% based on the total weight of the composition.

When (d) is present and is ethanol, (d) is suitably present in an amount of up to about 10%, preferably in an amount of about 2–5% based on the total weight of the composition.

When present, (e) is suitably present in an amount of up to 10%, preferably about 5% (e.g. ca. 6%), based on the total weight of the composition.

When present, components (d) and/or (e) will generally be introduced in partial replacement of component/ingredient (b+c). Thus where the compositions of the invention comprise (a)+(b+c)+(e) [but not (d)] and (e) is present in an amount of 6% by weight based on the total weight of the composition, (b+c) will generally be present in an amount of from about 74 to about 92%, preferably from about 69 to about 89% most preferably about 84% based on the total weight of the composition.

For the purposes of oral administration, the compositions of the invention in accordance with $B^1$ to $B^5$ above will preferably be put up in unit dosage form. In so far as the compositions are liquid this may be done by filling into a solid pharmaceutical unit dosage container such as a capsule, e.g. a hard or soft gelatin capsule, for direct oral administration or a phial or ampoule, e.g. for subsequent admixture with a drink-mixture, e.g. chocolate drink, prior to administration as currently practiced for the known cyclosporin "drink solution". Where the compositions of the invention are bi-phasic as hereinbefore described, the components may be homogenised to produce a uniform mixture prior to filling into the chosen dosage form, thus facilitating the filling procedure. Component (e) may then separate out from other components present to form a separate phase or layer, e.g. after closure of the unit dosage form. Most preferably the compositions of the invention are put up in soft gelatin capsule form.

In general: where unit dosage forms, e.g. of the type described above, are desired, components (a) and (b+c) are suitably present in the compositions of the invention in a ratio of from about 1:4 to about 1:50, preferably from about 1:5 to about 1:20, most preferably about 1:9 p.p.w. [(a):(b+c)].

When a component (d) is present and this is the trans-esterification product of a natural vegetable oil triglyceride and a polyalkylene polyol, components (d) and (b+c) are suitably present in a ratio of from about 1:1.25 to about 1:3.5, most preferably about 1:2 p.p.w. [(d):(b+c)]. When a component (d) is present and is the trans-esterification product of a natural vegetable oil triglyceride and a polyalkylene polyol, components (a), (b+c) and (d) are suitably present in a ratio of from about 1:9:0.1 to about 1:3.5:5.5, preferably from about 1:7:2 to about 1:5:4, most preferably about 1:6:3 p.p.w. [(a):(b+c):(d)].

When a component (d) is present and this is a component (e) as hereinafter described, especially an esterification product of caprylic and caproic acid with glycerol, components (d) and (b+c) are suitably present in a ratio of from 1:50 to about 1:1, preferably from about 1:45 to about 1:3.5 p.p.w. [(c):(b+c)]. When a component (d) is present and this is an esterification product of caprylic and caproic acid with glycerol, components (a), (b+c) and (d) are suitably present in a ratio of from about 1:9:0.2 to about 1:5:4, preferably from about 1:8.8:0.2 to about 1:7:2 p.p.w. [(a):(b+c):(d)].

When component (d) is present and is ethanol, components (d) and (b+c) are suitably present in a ratio of from about 1:8 to about 1:90 preferably from about 1:20 to about 1:45 p.p.w. [(d):(b+c)].

When a component (e) is present, components (a) and (e) are suitably present in a ratio of from about 1:0.1 to about 1:5, preferably from about 1:0.3 to about 1:1, most preferably about 1:0.5 p.p.w. [(a):(e)]. When a component (d) is present, components (a), (b) and (d) are suitably present in a ratio of from about 1:9:0.1 to about 1:8:1, preferably about 1:8.5:0.5 p.p.w. [(a):(b+c):(d)].

When components (d) and (e) are both present, and (d) is the trans-esterification product of a natural vegetable oil triglyceride and a polyalkylene polyol, components (a), (b+c), (d) and (e) are suitably present in a ratio of from about 1:9:0.1:0.1 to about 1:3:5:1, preferably from about 1:6.5:2:0.5 to about 1:4.5:4:0.5, most preferably about 1:5.5:3:0.5 p.p.w. [(a):(b+c):(d):(e)].

In an alternative and specific embodiment, compositions of the invention in accordance with $B^1$ to $B^5$ above may be put up in unit dosage from by compounding or admixture with an appropriate pharmaceutically acceptable base material such that the obtained product or admixture is capable of being formed into a solid unit dosage. In so far as the compositions of the invention may themselves be solid or semi-solid, e.g. when (b+c) comprises MAISINE or the like, particularly when (d) is absent, such products and admixtures are readily achievable. Suitable base materials include any of those known and commonly employed in the art and providing products and admixtures with the compositions of the invention capable of being formed, e.g. moulded, pressed, cast or otherwise shaped, into unit dosage form.

For the preparation of unit dosage forms in this particular manner, the compositions of the invention preferably comprise components (a) and (b+c) and, optionally (e), but not (d).

In contradistinction to compositions to be contained in an ampoule or the like, it is further preferred that compositions according to the invention and processed in this manner comprise components (a) and (b+c) in a ratio of from about 1:1 to about 1:10, preferably from about 1:1 to about 1:5, most preferably about 1:2.5 p.p.w. [(a):(b+c)].

Preferred base materials for use in accordance with this particular modification of the present invention comprise in particular natural fats, especially vegetable fats, for example cacao fat or cacao butter and conventional chocolate bases, e.g. couverture chocolate and mixtures thereof. Where a natural fat is employed the ratio of (a) to fat is preferably from about 1:0.5 to about 1:2, more preferably from about 1:1 to about 1:1.5, most preferably about 1:1.25 p.p.w. [(a):fat]. Where a chocolate base is employed the ratio of (a) to chocolate is preferably from about 1:10 to about 1:50, more preferably from about 1:10 to 1:30 and most preferably about 1:20 p.p.w. [(a):chocolate]. By compounding or admixture of a composition in accordance with the invention with a fat and chocolate, e.g. in the above described proportion, a product may be obtained in the form of a substantially homogenous mass which can be put up in unit dosage form, e.g. by pouring as a warm melt into an appropriate mould, e.g. as described in the following example 5, to provide a cyclosporin sweet meat, bon-bon or candy as unit dosage form.

Alternatively components (a) and (b+c) may be filled, optionally together with component (d), into a chocolate mantel, cover or capsule.

Unit dosage forms in accordance with $B^1$ to $B^5$ above suitably contain from about 25 to 500, more preferably about 50 to 300, especially 50, 100, 150 or 200 mg of component (a), e.g. of Ciclosporin, for administration e.g. 1× or from 2 to 3× daily.

Compositions in accordance with the present invention, e.g. in accordance with A or any one of $B^1$ to $B^5$ above, which comprise a component (e) as hereinbefore set forth, in particular comprising (e') a tenside having an HLB of at least 10, are of especial interest. In particular such compositions have been found to be surprisingly and unexpectedly well adapted to meet difficulties in the art hitherto encountered in relation to cyclosporin dosaging, e.g. as hereinbefore particularly discussed.

Accordingly, in an especially preferred embodiment, the present invention further provides:

C. A pharmaceutical composition comprising:
  a) a cyclosporin as active ingredient in a carrier medium comprising
  b) a fatty acid triglyceride,
  c) a glycerol fatty acid partial ester or propylene glycol (e.g. 1,2-propylene glycol) or sorbitol complete or partial ester, and
  e') a tenside having a hydrophilic-lipophilic balance (HLB) of at least 10.

In a series of specific embodiments the present invention also provides:

A composition as defined under C above, which composition:
  i) is free or substantially free of ethanol; or
  ii) comprises Ciclosporin or [Nva]$^2$-Ciclosporin as component (a); or
  iii) comprises components (a) and (e') in a ratio of 1: at least 1 p.p.w.

Provisos (i) to (iii) above are not mutually exclusive. Compositions in accordance with C complying with said provisos and in which components (b) and (c) comprise, or consist or consist essentially of the individual components of an ingredient or component (b+c) as defined under any one of $B^1$ to $B^3$ above, e.g. in which components (b) and (c) consist or consist essentially of the individual components of a trans-esterification product of a vegetable oil with glycerol, are of particular interest.

Component (a) is suitably present in the compositions as defined under C above in an amount of from ca. 2–20%, more preferably ca. 5–15% based on the total weight of components (a) to (c) and (e') inclusive. The preferred component (a) is Ciclosporin. A further preferred component (a) is [Nva]$^2$-Ciclosporin, also known as cyclosporin G.

Examples of suitable components (e') in the compositions as defined under C. above are:

e'.1 Reaction products of a natural or hydrogenated castor oil and ethylene oxide. Such products may be obtained in known manner, e.g. by reaction of a natural or hydrogenated castor oil with ethylene oxide, e.g. in a molar ratio of from about 1:35 to about 1:60, with optional removal of the polyethyleneglycol component from the product, e.g. in accordance with the methods disclosed in German Auslegeschriften 1,182,388 and 1,518,819. Especially suitable are the various liquid tensides available under the trade name CREMOPHOR. Particularly suitable are the products CREMOPHOR RH 40 having a saponification number of ca. 50–60, an acid number <1, an iodine number <1 a water content (Fischer) <2%, an $n_D^{60}$ of ca. 1.453–1.457 and an HLB of ca. 14–16; CREMOPHOR RH 60 having a saponification number of ca. 40–50, an acid number <1, an iodine number <1, a water content (Fischer) 4.5–5.5%, and an $n_D^{25}$ of ca. 1.453–1.457 and an HLB of ca. 15–17; and CREMOPHOR EL having a molecular weight (by steam osmometry) of ca. 1630, a saponification number of ca. 65–70, an acid number of ca. 2, an iodine number of ca. 28–32 and an $n_D^{25}$ of ca. 1.471. Also suitable for use in this category are the various tensides available under the trade name NIKKOL, e.g. NIKKOL HCO-40 and HCO-60. The said product NIKKOL HCO-60 is a reaction product of hydrogenated castor oil and ethylene oxide exhibiting the following characteristics: acid value ca. 0.3; saponification number of ca. 47.4; hydroxy value of ca. 42.5; pH (5%) of ca. 4.6; color APHA=ca. 40; m.p.=ca. 36.0° C.; freezing point=ca. 32.4° C.; H$_2$O content (%, KF)= 0.03.

e'.2 Polyoxyethylene-sorbitan-fatty acid esters, e.g. mono- and tri-lauryl, palmityl, stearyl and oleyl esters, e.g. of the type known and commercially available under the trade name TWEEN (c.f. Fiedler, "Lexikon der Hilfstoffe", 2nd revised and expanded edition (1981), Vol.2, p.p. 972–975) including the products TWEEN
  20 [polyoxyethylene(20)sorbitanmonolaurate],
  40 [polyoxyethylene(20)sorbitanmonopalmitate],
  60 [polyoxyethylene(20)sorbitanmonostearate],
  65 [polyoxyethylene(20)sorbitantristearate],
  85 [polyoxyethylene(20)sorbitantrioleate],
  21 [polyoxyethylene(4)sorbitanmonolaurate],
  81 [polyoxyethylene(5)sorbitanmonooleate].

Especially preferred products of this class for use in the compositions of the invention are the above products TWEEN 40 and TWEEN 80.

- e'.3 Polyoxyethylene fatty acid esters, for example polyoxy- ethylene stearic acid esters of the type known and commercially available under the trade name MYRJ (c.f. Fiedler, loc. cit., 1, p.228); an especially preferred product of this class for use in the compositions of the invention is the product MYRJ 52 having a $D^{25}$=ca. 1.1., m.p.=ca. 40°–44° C., an-HLB value=ca. 16.9., an acid value=ca. 0–1 and a saponification no.= ca. 25–35.

- e'.4 Polyoxyethylene-polyoxypropylene co-polymers and block co-polymers, e.g. of the type known and commercially available under the trade names PLURONIC, EMKALYX POLOXAMER (c.f. Fiedler, loc. cit., 2, p.p. 720–723). An especially preferred product of this class for use in the compositions of the invention is the product PLURONIC F68, having an m.p.=ca. 52° C. and a molecular weight of ca. 6800–8975. A further preferred product of this class for use in the compositions of the invention is the product POLOXAMER 188.

- e'.5 Dioctylsuccinate or di-[2-ethylhexyl]-succinate (c.f. Fiedler, loc. cit., 1, p.p. 307).

- e'.6 Phospholipids, in particular lecithins (c.f. Fiedler, loc. cit., 2, p.p. 559–560). Lecithins suitable for use in the compositions of the invention include, in particular, soya bean lecithins.

- e'.7 Propylene glycol mono- and di-fatty acid esters such as propylene glycol dicaprylate (also known and commercially available under the trade name MIGLYOL 840), propylene glycol dilaurate, propylene glycol hydroxystearate, propylene glycol isostearate, propylene glycol laurate, propylene glycol ricinoleate, propylene glycol stearate and so forth (c.f. Fiedler, loc. cit., 2, p.p. 760 et seq.).

- e'.8 Sodium lauryl sulfate.

The ratio of components (a):(e') in the compositions in accordance with C. above is suitably of the order of 1:1 to 25 p.p.w., more preferably 1:1.25 to 20 p.p.w., yet more preferably 1:1.5 to 8 or 10 p.p.w. e.g. ca. 1:2 to 5 p.p.w. Most preferably the ratio of components (a):(e') is 1: at least 2 p.p.w. Component (a) is thus suitably present in the compositions of the invention in an amount e.g. of from ca. 20–50%, more preferably 25–40%, by weight based on the total weight of components (a) and (e').

Components (b) and (c) in compositions in accordance with C. above may comprise or consist or consist essentially of the individual components (b) and (c) of a single ingredient, e.g. single material or product. Examples of ingredients comprising both components (a) and (b) suitable for use in the present invention include for example known mixed fatty acid tri-glyceride and fatty acid mono-/di-glyceride products. Suitable products of this type include, in particular, transesterification products of vegetable oils with glycerol, propylene glycol (e.g. 1,2-propylene glycol) or sorbitol e.g. as hereinbefore described in relation to definitions $B^1$ to B3 above.

Suitable components of this type thus include any ingredient (b+c) as hereinbefore described, in particular products of the type MAISINE and SORBITO GLYCERIDES.

In the case of compositions in accordance with C. above of which the components (b) and (c) consist or consist essentially of the individual components (b) and (c) of a single ingredient, e.g. of which the components (b) and (c) are comprised entirely or substantially entirely of transesterification products as hereinbefore described above, the ratio of (a):(b+c) is suitably of the order of 1:0.75–35, preferably 1:1–25 p.p.w., more preferably the ratio is of the order of 1:3–10, especially ca. 1:6 p.p.w.. Where only ingredients comprising both (b) and (c) are employed, (b+c) are thus suitably present in the compositions of the invention in an amount of from ca. 15–70%, more preferably ca. 20–50% by weight, based on the total weight of components (a) to (c) and (e') inclusive.

To enable combination of components (b) and (c) in the compositions of the invention, e.g. as defined under C. above, in preferred proportion as hereinafter described, component (b) in the compositions of the invention will however preferably comprise at least one ingredient definable as a fatty acid triglyceride as such, e.g. material or product, which is, or which consists or consists essentially of components (b) as hereinbefore defined (i.e. fatty acid triglycerides), e.g. which comprises at least 75%, preferably at least 90%, more preferably at least 95% by weight of components (b). Component (c) in the compositions of the invention will also preferably comprise at least one ingredient which is definable as a glycerol fatty acid partial ester or propylene glycol or sorbitol complete or partial ester as such, e.g. which is or which consists or consists essentially of components (c) as hereinbefore defined, e.g. which comprises at least 75%, preferably at least 90%, more preferably at least 95% by weight of said components (c).

More preferably components (b) and (c) in the compositions of the invention, e.g. as defined under c. above, will comprise separate ingredients combinable in selected proportion [(b):(c)] as hereinafter described. With respect to the components (b) and (c), the compositions of the invention will thus most preferably comprise a bi-partite combination of ingredients complying with definition (b) and of ingredients complying with definition (c), e.g. a combination of a first ingredient or ingredients consisting or consisting essentially of components (b) and of a second ingredient or ingredients consisting or consisting essentially of components (c).

Suitable components (b) include both saturated (including hydrogenated) and unsaturated fatty acid tri-glycerides, in particular animal or vegetable oils. The fatty acid constituents of components (b) suitably include, saturated or mono-, di- or poly-unsaturated acids having e.g. chain lengths of from 6 to 22 carbon atoms. Especially suitable for use in accordance with the invention are fatty acid triglycerides having a high content of unsaturated fatty acid constituents in particular mono-, di- and poly-unsaturated fatty acids having at least 16 carbon atoms, preferably 18 carbon atoms or more, in particular having a high oleic, linoleic or linolenic fatty acid constituent content. Of particular interest are fatty acid triglycerides having a linoleic and/or linolenic acid constituent content of at least 45%, preferably at least 60% and up to 65 or 80%, e.g. where super-refined oils are used.

A first group of fatty acid triglycerides suitable for use in accordance with the invention includes saturated $C_{6-12}$ fatty acid vegetable oil triglycerides, e.g. caprylic-capric acid triglycerides. Examples of ingredients suitable as components (b) thus include fractionated vegetable oils, e.g. fractionated coconut oils such as are known and commercially available under the trade name MIGLYOL (c.f. Fiedler, loc. cit., 2, 615 and 616), including MIGLYOL 810, a fractionated coconut oil, caprylic-capric acid triglyceride having a molecular weight of ca. 520 and a fatty acid constitution=$C_6$ max. ca. 2%, $C_8$ ca. 65–75%, $C_{10}$ ca. 25–35%, $C_{12}$ max. ca.

2%. MIGLYOL 810 has the following further physical characteristics: $\alpha_D^{20}$=1.4490–1.4510, acid no.=max. 0.1, saponification no.=ca. 340–360, iodine value=max. 1. Especially preferred is MIGLYOL 812, a fractionated coconut oil, caprylic-capric acid triglyceride having a molecular weight of ca. 520, and a fatty acid constitution=$C_6$, max. ca. 3%, $C_8$ ca. 50–65%, $C_{10}$ ca. 35–40%, $C_{12}$ max. ca. 5%. MIGLYOL 812 has the following further physical characteristics: $\alpha_D^{20}$=1.4480–1.4500, saponification no.=ca. 330–345, iodine value=max. 1.

Further ingredients of similar class suitable for use as components (b) include those known and commercially available under the trade name ESTASAN, for example ESTASAN GT 8–60 and GT 8–65. ESTASAN GT 8–60 is a vegetable oil fatty acid triglyceride in which the fatty acid components are comprised chiefly of saturated $C_{8-10}$ fatty acids, in particular caprylic and capric acids. Fatty acid constitution=caproic ($C_6$) max. ca. 3%, caprylic ($C_8$) max. ca. 50–65%, capric ($C_{10}$) max. ca. 35–45%, lauric ($C_{12}$) max. ca. 3%. ESTASAN GT 8–60 exhibits the following additional physical characteristics: saponification no.=ca. 325–345, iodine no.=max. ca. 1, acid value=max. ca. 0.1, $\alpha_D^{20}$=ca. 1.448–1.451. ESTASAN GT 8–65 is also a vegetable oil fatty acid triglyceride, comprised chiefly of saturated $C_{8-10}$ fatty acids, in particular caprylic and capric acids. Fatty acid constitution=caproic max. ca. 1%, caprylic min. ca. 65%, capric ca. 25–35%, lauric max. ca. 1%.

Yet further ingredients of this class are those known and commercially available under the trade name MYRITOL, for example MYRITOL 318 [c.f. Fiedler, loc. cit., 2, p.p. 635–636]. MYRITOL 318 is a caprylic/capric acid triglyceride having a saponification no.=ca. 340–350, an iodine no.=ca. 0.5 and an $n_D^{20}$=ca. 1.448–1.450.

Further ingredients suitable for use as components (b) include, e.g. vegetable oils such as corn oils, almond oils, kernel oils (for example apricot kernel oils), avocado oils, babassu oils, higher fatty acid coconut oils, primrose oils, grapeseed oils, menhaden oils, olive oils, orange roughy oils, peanut oils, safflower oils, sesame oils, soybean oils and wheat-germ oils as well as animal oils such as fish oils, e.g. fish liver oils, for example shark oils, and mink oils. Refined oils of any of the above types are of particular interest for use in accordance with the present invention, in particular refined plant oils, e.g. having the following approximate oleic/linoleic/linolenic acid constituent content:

| OLEIC ACID | LINOLEIC ACID | LINOLENIC ACID | EXAMPLE |
| --- | --- | --- | --- |
| ca. 9% | ca. 68% | ca. 15% | evening primrose |
| ca. 27% | ca. 64% | — | grapeseed |
| ca. 4% | ca. 13% | ca. 76% | safflower |
| ca. 5% | ca. 40% | ca. 47% | sesame |
| ca. 25% | ca. 54% | ca. 6% | soybean |
| ca. 14% | ca. 58% | ca. 8% | wheat-germ |

Component (c) for use in compositions of the invention, e.g. as defined under C. above, suitably comprises a glycerol fatty acid partial ester, i.e. a fatty acid mono- or di-glyceride, or acetylated derivative thereof. Ingredients suitable for use as component (c) will preferably be free or substantially free of any fatty acid tri-glyceride component, e.g. contain less than 25%, preferably less than 10%, more preferably less than 5%, e.g. less than 1 or 2% fatty acid triglycerides.

Components (c) as aforesaid include both symmetric mono- and di-glycerides (i.e. β-monoglycerides and $\alpha,\alpha^1$-diglycerides) as well as asymmetric mono- and di-glycerides (i.e. α-monoglycerides and α,β-diglycerides) and acetylated derivatives thereof. They also include both uniform glycerides (i.e. in which the fatty acid constituent is composed primarily of a single fatty acid) as well as mixed glycerides (i.e. in which the fatty acid constituent is composed of various fatty acids) and acetylated derivatives thereof.

The fatty acid constituent of components (c) may include both saturated and unsaturated fatty acids having a chain length of from 6 to 22 carbon atoms. Preferably the fatty acid constituent will predominantly comprise saturated or unsaturated fatty acids having a chain length of from 8 to 18 carbon atoms, in particular 8, 10 or 14 to 18, e.g. 16 or 18 carbon atoms. Especially suitable are mono- and di-glycerides in which the fatty acid constituent is comprised predominantly of one or more members selected from the group consisting of caprylic, capric, linolenic, palmitic, stearic and oleic acids.

Particularly preferred for use as components (c) are ingredients comprising mono- and di-glycerides, wherein the mono-/di-glyceride content is at least 50%, preferably at least 60%, more preferably at least 75% by weight, and acetylated derivatives thereof. Examples of appropriate ingredients for use as components (c) are:

c.1 Fatty acid mono- and di-glycerides, e.g. products obtained or obtainable by esterification of from about 50 to 75, e.g. about 60, parts by weight, and from about 50 to about 25, e.g. about 40, parts by weight of capric acid with glycerol, and comprising, or consisting mainly or essentially of caprylic/capric acid mono- and di-glycerides. Examples of such products include those known and commercially available under the trade name IMWITOR (c.f. Fiedler, loc. cit., 1, p. 491), in particular: caprylic and capric acid mono- and di-glycerides such as IMWITOR 742. IMWITOR 742 is the esterification product of a mixtrue of ca. 60 p.p.w. caprylic acid and ca. 40 p.p.w. capric acid with glycerol. It comprises ca. 40 to 50% or more monoglycerides. It is a yellowish crystalline mass, liquid at ca. 26° C. It exhibits the following, additional characterising data—acid value=max. ca. 2%, iodine value=max. ca. 1.0, saponification no. ca. 250–280, free glycerol content=max. ca. 2%, unsaponifiables=0.3% max., peroxide no.=max 1; and stearic acid mono-glycerides such as IMWITOR 191, which comprises at least 90% mono-glycerides as aforesaid and exhibits the following, additional characterising data—m.p.=ca. 63°–66° C., acid value=max. ca. 3, saponification no.=ca. 160–170, iodine value=max. ca. 3, free glycerol content=max. ca. 2%, and IMWITOR 960K which comprises 30–40% monoglycerides as aforesaid and exhibits the following, additional characterising data—m.p. rising from ca. 56° to ca. 60° C., saponification no.=ca. 155–170, acid value=max. ca. 3, iodine value=max. ca. 3, free glycerol content=max. ca. 4%.

c.2 Fatty acid mono- and di-glycerides as commercially available under the trade name CUTINA (c.f. Fiedler, loc. cit., 1, p.p. 263 and 264): in particular palmitic and stearic acid mono- and di-glycerides such as CUTINA MD-A, which comprises mono- and di-glycerides as aforesaid and exhibits the following characterising data—acid value=max. ca. 8, saponification no.=ca. 160–170; and stearic acid mono-glycerides such as CUTINA GMS which comprises mono-glycerides as aforesaid and exhibits the following characterising data—m.p.=ca. 54°–60° C., acid value=max. ca. 2, saponification no=ca. 162–173, iodine value=max. ca. 2.

c.3 Fatty acid mono-glycerides as commercially available under the trade name MYVEROL (c.f. Fiedler, loc. cit., 2, 637), in particular $C_{18}$ fatty acid, e.g. linolenic acid, mono-glycerides such as MYVEROL 18–92, which comprises at least 90% mono-glycerides as aforesaid and exhibits the following additional characterising data: acid value=max. ca. 3.0, diglyceride content= max. ca. 5%, free glycerol content=max. ca. 1.2%.

c.4 Fatty acid mono-glycerides as commercially available under the trade name MYVAPLEX (c.f. Fiedler, loc. cit., 2, 637), in particular stearic acid mono-glycerides such as those of the MYVAPLEX 600 series, e.g. MYVAPLEX 600P which comprises ca. 94–90% mono-glycerides as aforesaid and exhibits the following additional characterising data—m.p.=ca. 73° C., density=ca. 0.92 g/cm³ at 80° C.

c.5 Fatty acid mono-glycerides as commercially available under the trade name ESTAGEL, for example ESTA-GEL G-18 which is comprised primarily of $C_{16-18}$ fatty acid mono-glycerides in particular palmitic and stearic acid mono-glycerides. The α-monoglyceride content of ESTAGEL G-18 is min. ca. 40%. Further characterising data: acid value=max. ca. 2, saponification no.=ca. 162–173, iodine no.=max. ca. 3, free glycerol content= max. ca. 6%.

c.6 Acetylated fatty acid mono- and di-glycerides such as commercially available under the trade name MYVACET (c.f. Fiedler, loc. cit.,2, p.p. 636–637), in particular mono- and di-acetylated fatty acid mono-glycerides, for example mono- and di-acetylated stearic acid mono-glycerides such as: MYVACET 9–40 which has the following characterising data—$\alpha_D^{50}$=ca. 1.4468–1.4476, m.p.=ca. 5° C., acid value=max. ca. 1.5, saponification no.=ca. 375–385; and MYVACET 9–45 which has the following characterising data— $\alpha_D^{50}$=ca. 1.4465–1.4475, m.p.=ca. 8°–12.4° C., acid value=ca. 1.5, saponification no.=ca. 375–385.

Further components (c) which are of particular utility, are mixed glycerol fatty acid partial esters and propylene glycol complete and partial esters, e.g. products comprising fatty acid mono- and di-glycerides and propylene glycol fatty acid mono- and di-esters. Examples of such components (c) include:

c.7 Fatty acid mono- and di-glycerides/propylene glycol fatty acid mono- and di-esters as commercially available under the trade name ATMOS [c.f. Fiedler, loc. cit., 1, p. 156], in particular ATMOS 300 in which the fatty acid moieties are comprised principally of oleic acid residues and ATMOS 150 in which the fatty acid moieties are comprised principally of stearic acid residues.

c.8 Fatty acid mono- and di-glycerides/propylene glycol fatty acid mono- and di-esters as commercially available under the trade name ARLACEL [c.f. Fiedler, loc. cit., 1, p.p. 143–144] in particular ARLACEL 186 in which the fatty acid moieties are comprised principally of oleic acid residues.

Components (b) and (c) are preferably present in the compositions of the invention, e.g. as defined under C. above, in a ratio of about 1:0.02 to 3.0 p.p.w. More preferably the ratio of components (b):(c) is of the order of 1:0.1 to 2.5 p.p.w., most preferably 1:0.25–1.25 p.p.w. When components (b) and (c) in the compositions of the invention, e.g. compositions C, comprise separate ingredients, e.g. as described above, the said ingredients will thus suitably be employed in the same relative ratios. The amount of components (b) in the compositions of the invention as defined under C. above is thus suitably of the order of from 10–50%, preferably 20–40% by weight, based on the total weight of components (a) to (c) and (e') inclusive, and the amount of components (c) in said compositions is suitably of the order of from 1–30%, preferably 10–25% by weight, based on the total weight of components (a) to (c) and (e') inclusive.

The ratio of components (a):(b) plus (c) in the compositions of the invention, e.g. as defined under C, is suitably of the order of 1:0.5 to 40 p.p.w. Preferably, the ratio of (a):(b) plus (c) is about 1:1 to 35, more preferably about 1:1.5 to 30 p.p.w., most preferably about 1:2 to 6.

In accordance with the foregoing the present invention also provides

D. A pharmaceutical composition as defined under C above comprising at least one ingredient which consists or consists essentially of, a component or components as defined under (b) above;

E. A pharmaceutical composition as defined under C above comprising at least one ingredient which consists or consists essentially of a component or components as defined under (c) above;

F. A pharmaceutical composition as defined under C above in which components (a) and (b) comprise separate ingredients.

The compositions of the invention, e.g. as defined under any of C to F above, may include further components, for example thickening agents, granulating agents, dispersing agents, flavouring and/or colouring agents or anti-microbial agents etc . . . as required. They may also include polymeric thickening agents to permit processing into a solid or semi-solid mass suitable for tabletting or forming into granules.

The compositions of the invention, in particular as defined under any of C to F above, will suitably include anti-oxidants to improve shelf-life, for example butyl-hydroxy-toluene (or BHT), butyl-hydroxy-anisole (or BHA), ascorbyl palmitate, ascorbic acid, citric acid or α-tocopherol-acetate.

In particular the compositions of the invention will suitably comprise one or more stabilizers or buffering agents, e.g. to prevent degradation of component (a) during processing or on storage. Such stabilizers may include acid stabilizers such as citric acid, acetic acid, tartaric acid or fumaric acid as well as basic stabilizers such as potassium hydrogen phosphate, glycine, lysine, arginine or tris (hydroxymethyl)aminomethane.

Such stabilizers or buffer agents will appropriately be added in an amount sufficient to achieve or maintain a pH within the range of from about 5 to 7, more preferably between 6 and 7.

When components (b) and (c) in the compositions of the invention are comprised of a single ingredient which is the trans-esterification product of a vegetable oil with glycerol, the compositions of the invention will preferably be subject to proviso (i) as set forth under C. above, i.e. they will be free or substantially free of ethanol. Suitably they will be free or substantially free of any further component serving as a diluent or as a solvent medium for component (a), e.g. free of any such diluent or solvent other than a component (b), (c) or (b+c) as hereinbefore described.

While proviso (i) is applied above in a specific instance, compositions in accordance with the invention which are free or substantially free of ethanol are in general preferred. Compositions in accordance with the invention which are free or substantially free of any further component serving as a diluent or as solvent medium for (a), are also, in general, preferred. In a yet further series of embodiments the present invention thus also provides:

G. A pharmaceutical composition as defined under any one of (A) to (F) above which is free, or substantially free, of ethanol; and H. A pharmaceutical composition as defined under any one of (A) to (F) above which is free or substantially free of any further component serving as a diluent or as solvent medium for component (a).

Compositions as aforesaid suitably comprise less than 2%, more suitably from 0 to 0.5 or 1% by weight ethanol, based on the total weight of the component ingredients. Compositions as aforesaid suitably comprise less than 20%, more preferably less than 10%, e.g. from 0 to 2.5 or 5.0% by weight further components serving as diluent or as solvent medium for component (a). Specific compositions in accordance with the present invention are pharmaceutical compositions as defined under any one of A. to H. above consisting, or consisting essentially, of components (b), (c) and (e)/(e') as carrier medium for (a), i.e. exclusive of any thickening, granulating, dispersing, flavouring, colouring, stabilizing agents or the like excipients that may also be present, and which are present as additives to the carrier medium.

By components serving as diluents are in particular to be understood, components serving to reduce the viscosity/increase the fluidity of the compositions of the invention. By components serving as solvent medium for (a) are in particular to be understood co-solvents or other materials which enhance the solubility of components (a) in the compositions of the invention. Examples of such components are, in particular, solvent or diluent components having an HLB of less than 10, for example, trans-esterification products of natural vegetable oil triglycerides and polyalkylene polyols such as known and commercially available under the trade name Labrafil and ethanol.

Compositions in accordance with the invention may be applied in dosage form suitable for administration by any appropriate means, e.g. in the form of creams, gels or the like for topical or occular administration, or in the form of granules, tablets, capsules, drink-solutions or the like for oral administration or in a form suitable for intra-lesional application, e.g. in the treatment of psoriasis. Preferably however the compositions of the invention will be administered orally. In a preferred embodiment the invention accordingly provides a composition as hereinbefore defined in a form appropriate or adapted for oral administration, in particular in oral unit dosage form. Especially suitable unit dosage forms for oral administration include encapsulated forms, e.g. soft or hard gelatin encapsulated forms.

Oral unit dosage forms in accordance with the invention, in particular in accordance with any of definitions C to F above, will suitably comprise from 5 to 200 mg, more preferably from 20 to 100 mg, e.g. ca. 25, 50 or 100 mg component (a), e.g. for administration 2–5×daily.

In addition to the foregoing the present invention also provides a process for the production of pharmaceutical compositions as hereinabove defined and described which process comprises intimately admixing components (a), (b), (c) or (b+c) and, when present, (d) and/or (e)/(e') thereof.

In a preferred aspect the present invention provides a process as aforesaid, which process comprises intimately admixing a component (a) with a first ingredient (b) which consists or consists essentially of one or more fatty acid triglycerides and a second ingredient (c) which comprises a glycerol fatty acid partial ester or propylene glycol or sorbitol complete or partial ester, or with a first ingredient (b) which comprises a fatty acid triglyceride and a second ingredient (c) which consists or consists essentially of one or more glycerol fatty acid partial esters and/or propylene glycol and/or sorbitol complete or partial esters, and with (e') a tenside having a hydrophilic-lipophilic balance of at least 10.

In a more preferred aspect the present invention provides a process as aforesaid, which process comprises intimately admixing a component (a) with a first ingredient (b) which consists or consists essentially of one or more fatty acid triglycerides, a second ingredient (c) which consists or consists essentially of one or more glycerol fatty acid partial esters and/or propylene glycol and/or sorbitol complete or partial esters, and (el) a tenside having a hydrophilic-lipophilic balance of at least 10.

The following examples are illustrative of the manufacture of compositions in accordance with the present invention:

EXAMPLE 1

A composition is prepared by intimate admixture of the following components in the indicated relative amounts.

| COMPONENT | AMOUNT | |
|---|---|---|
| a) Ciclosporin | 100 mg | (=ca. 10.5%) |
| b + c) MAISINE | 550 mg | (=ca. 57.8%) |
| d) LABRAFIL M 2125 | 300 mg | (=ca. 33.5%) |
| TOTAL | 950 mg | |

The components are thouroughly admixed in conventional manner and the obtained mixture filled into standard soft gelatin capsules containing 950 mg composition per capsule.

EXAMPLE 2

Example 1 is repeated but using the following components in the indicated relative amounts:

| COMPONENT | AMOUNT | |
|---|---|---|
| a) Ciclosporin | 100 mg | (=ca. 10.5%) |
| b + c) MAISINE | 490 mg | (=ca. 52%) |
| d) LABRAFIL M 2125 | 300 mg | (=ca. 31.5%) |
| e') CREMOPHORE RH40 | 60 mg | (=ca. 6.3%) |
| TOTAL | 950 mg | |

The composition is filled into soft gelatin capsules containing 950 mg composition/capsule. Subsequent to sealing component (d) separates out from other components present.

EXAMPLE 3

Example 1 is repeated but using the following components in the indicated relative amounts:

| COMPONENT | AMOUNT | |
|---|---|---|
| a) Ciclosporin | 100 mg | (=ca. 10.5%) |
| b + c) MAISINE | 850 mg | (=ca. 89.5%) |

The composition is filled into soft gelatin capsules containing 950 mg composition/capsule.

EXAMPLE 4

Example 1 is repeated but using the following components in the indicated relative percentages.

| COMPONENT | % |
|---|---|
| a) (Dihydro-MeBmt)$^1$—(Val)$^2$-Ciclosporin (also known as dihydrocyclosporin D) | 15–25% |
| b + c) MAISINE | 40–60% |
| c) IMWITOR 742 | 10–40% |
| d) Ethanol | 2–5% |

(IMWITOR 742 = a glycerine ester available from Dynamite Nobel AG, Troisdorf-Obelar, SN).

The quantitiy of a) required for a single dosage (ca. 100–200 mg) is dissolved in the remaining components using conventional techniques to give a solution for filling into a soft gelatin capsule.

EXAMPLE 5

| COMPONENT | QANTITY (g) |
|---|---|
| a) Ciclosporin + | 4.0 |
| 7% excess | 0.028 |
| | 4.028 |
| b + c) MAISINE | 10.0 |
| x) Cacao fat | 5.0 |
| y) Chocolate base (couverture chocolate) | 80.97 |
| Total | 99.998 |

Components (x) and (y) are mixed thoroughly on a water bath at 40° C. Component (a) is dissolved in component (b+c) under a nitrogen atmosphere and the obtained mixture added to the mixture of (x)+(y). The whole is mixed thoroughly on a water bath at 40° C. and then filled into moulds in 2,500 mg portions, each portion containing 150 mg cyclosporin A. The moulds are stored overnight in a refrigerator and the obtained unit dosage forms sealed in individual plastic sachets.

EXAMPLE 6

| INGREDIENT | QUANTITY (mg) |
|---|---|
| a) Cyclosporin (e.g. Ciclosporin) | 50.00 |
| b) MIGLYOL 812 | 100.00 |
| c) MYVEROL 18-92 | 100.00 |
| e') CREMOPHORE RH 40 | 50.00 |

(a)–(e') are intimately admixed in the indicated proportions in conventional manner and the obtained mixture filled into soft or hard gelatin capsules each containing 50 mg Cyclosporin.

EXAMPLE 7

Soft or hard gelatine capsules each comprising the following indicated ingredients in the indicated amounts, are prepared analogously to Example 1:

| | INGREDIENT | QUANTITY (mg) |
|---|---|---|
| 7a | a) Cyclosporin (e.g. Ciclosporin) | 50.00 |
| | b) MIGLYOL 812 | 100.00 |
| | c) IMWITOR 742 | 100.00 |
| | e') CREMOPHORE RH 40 | 100.00 |
| 7b | a) Cyclosporin (e.g. Ciclosporin) | 50.00 |
| | b + c) MAISINE | 300.00 |
| | e') CREMOPHORE RH 40 | 100.00 |
| 7c | a) Cyclosporin (e.g. Ciclosporin) | 50.00 |
| | b) Soyabean oil | 150.00 |
| | c) MYVEROL 18-92 | 50.00 |
| | e') EMULGIN R040* | 250.00 |
| 7d | a) Cyclosporin (e.g. Ciclosporin) | 50.00 |
| | b) Sesame oils | 150.00 |
| | c) IMWITOR 900K | 125.00 |
| | e') EMULPHOR EL-719* | 150.00 |
| 7e | a) Cyclosporin (e.g. Ciclosporin) | 50.00 |
| | b) MYRITOL 318 | 75.00 |
| | c) ESTAGEL G-18 | 100.00 |
| | e') PLURONIC F68 | 175.00 |
| 7f | a) Cyclosporin (e.g. Ciclosporin) | 50.00 |
| | b) ESTASAN GT 8-60 | 130.00 |
| | c) ARLACEL 186 | 75.00 |
| | e') TWEEN 80 | 125.00 |
| 7g | a) Cyclosporin (e.g. Ciclosporin) | 50.00 |
| | b) + c) MAISINE | 100.00 |
| | c) MYVEROL 18-92 | 200.00 |
| | e') CREMOPHORE RH40 | 100.00 |
| 7h | a) Cyclosporin (e.g. Ciclosporin) | 50.00 |
| | b) MIGLYOL 812 | 100.00 |
| | c) MYVEROL 18-92 | 200.00 |
| | e') CREMOPHORE RH40 | 100.00 |

[*c.f. Fiedler, loc. cit. 1, p. 344]

The compositions obtained in accordance with examples 1 to 7 are suitable for administration for the prevention of transplant rejection or in the treatment of auto-immune disease, e.g. on administration of from 1 to 5 unit dosages, e.g. capsules, daily. Equivalent compositions may be prepared substituting any other Cyclosporin, e.g. [Nva]$^2$-Ciclosporin, as component (a) in the same or equivalent amount.

Utility of compositions in accordance with the invention may be shown in animal or clinical trials, for example performed as follows:

BIOAVAILABILITY STUDY FOR COMPOSITIONS IN ACCORDANCE WITH THE INVENTION IN THE DOG

STUDY I

Test Dosage Forms

A. Unit dosages obtained in accordance with the above example 5, each unit dosage comprising 100 mg Ciclosporin.

B. Hard-gelatin capsules, each capsule containing 50 mg Ciclosporin compounded with 50 mg ethanol, 150 mg LABRAFIL M. 1944 CS and 212.5 mg olive oil (=currently commercially available Ciclosporin "drink solution").

Prepartions A and B are administered to male beagle dogs in randomised, cross-over sequence. Both preparations are administered directly into the oesophagus and swallowed without chewing, and aministration is followed by washing out of the oesophagus with 10 ml water delivered as a spray. Preparation A is administered in single dosages. Preparation B is administered in double dosage (=100 mg cyclosporin A).

2 ml blood samples are taken prior to administration (control) and subsequent to administration at intervals of 0.5, 1,2,3,4,6,7,12,24,31,48 and 72 hours.

Blood samples are frozen at −20° C. immediately after collection and stored for analysis. Assay is effected by standard cyclosporin A radioimmunoassay technique employing obtained blood samples in 2μ aliquots, assay being effected 2×/sample. Standard curves for the assay are prepared for each individual dog. For characterisation of the release kinetics, average concentration for each sample, standard variation, average error and overall average concentration are calculated.

Variance analysis (p=1%) indicates a significance difference in average-AUC (area under curve) value between compositions A and B, with bio-availability for composition A being superior of that for composition B.

Advantageous bio-availability levels of the same or equivalent order may be demonstrated in analogous trials to the above employing compositions of the invention in soft-gelatin capsule form, e.g. compositions prepared in accordance with the preceeding examples 1 through 4 or 6 or 7.

STUDY II

Groups of 8 beagle dogs (male, ca. 11–13 kg) are used. Animals receive no food within 18 hours of administration of test composition but are allowed free access to water until administration. Test composition is administered by gavage, followed by 20 ml NaCl 0.9% solution. The animals are allowed free access to food and water three hours after administration of test composition.

2 ml blood samples (or 5 ml for the blank) are taken from the vena saphena and collected in 5 ml plastic tubes containing EDTA at −15min. (blank), 30 min., and 1, 1.5, 2, 3, 4, 6, 8, 12 and 24 hours post administration. Blood samples are stored at −18° C. pending assay.

Blood samples are analysed by RIA. Areas under the blood drug concentration versus time curves are calculated by the trapezoidal rule. Analysis of variance is performed with respect to AUC (area under curve), Cmax (maximum concentation) and Tmax (time of maximum).

Calculated average AUC (in ng hr./ml$^{-1}$) and Cmax (in ng/ml$^{-1}$) values from individual trial runs together with calculated variation in response between test animals receiving the same test composition (CV), demonstrate high bioavailability (AUC and Cmax.) coupled with relatively low variability in subject response both for AUC and Cmax for compositions in accordance with the invention, e.g. in accordance with example 6 above, as compared e.g. with results for the known SANDIMMUN drink solution composition (e.g. as described in relation to the following CLINICAL TRIAL) administered at the same Ciclosporin dosage level.

CLINICAL TRIAL

The advantageous properties of the compositions of the invention on oral administration may also be demonstrated in clinical trials, e.g. performed as follows:

Trial subjects are adult volunteers, e.g. professionally educated males of from 30 to 55 years. Trial groups suitably comprise 12 subjects.

The following inclusion/exclusion criteria are applied:
Inclusion: Normal screening ECG; normal blood-pressure and heart rate; body weight=50–95 kg.
Exclusion: Clinically significant intercurrent medical condition which might interfere with drug absorption, distribution, metabolism, excretion or safety; symptoms of a significant clinical illness in the two-week pre-trial period; clinically relevant abnormal laboratory values or electrocardiogram; need for concomitant medication during the entire course of the study; administration of any drug known to have a well-defined potential toxicity to a major organ system within the previous 3 months; administration of any investigational drug within 6 weeks prior to entry into the trial; history of drug or alcohol abuse; loss of 500 ml or more blood within the past 3 month period; adverse drug reaction or hypersensitivity; history of allergy requiring drug therapy; Hep.-B/HIV-positive.

Complete physical examination and ECG is performed pre- and post-trial. The following parameters are evaluated within 1-month periods pre- and post-trial:

Blood:—red blood cell count, haemoglobin, hematocrit, erythrocyte sedimentation, white blood cell count, smear, platelet count and fasting glucose;

Serum/plasma—total protein and electrophoresis, cholesterol, triglycerides, Na$^+$, K$^+$, Fe$^{++}$, Ca$^{++}$, Cl$^-$ creatinine, urea, uric acid, SGOT, SGPT, alkaline phosphatase, total bilirubin, α-amylase; Urine—pH, microalbumin, glucose, erythrocytes, ketone bodies, sediment.

Creatinine clearance is also determined 1-month prior to trial entry.

Subjects each receive trial compositions in randomised sequence. Compositions are administered orally, once to a total dose of 150 mg cyclosporin, e.g. Ciclosporin, and at least 14 days are allowed between each administration.

Administration is performed in the morning after an overnight fast of 10 hrs. with only water allowed. Only caffein-free beverages are permitted within the 24 hr. period following administration. Subjects are not allowed to smoke within the 12 hr. period following administration. Subjects receive a standardised lunch 4 hrs. following administration.

Blood samples (2 ml) are taken 1 hr. prior to administration and post-administration at 0.25, 0.5, 1, 1.5, 2, 2.5, 3, 3.5, 4, 4.5, 5, 6, 9, 12, 14, 24, 28 and 32 hrs. For determination of creatinine 2 ml blood samples are taken immediately prior to administration and at 12, 24 and 48 hrs. post-administration. Samples for cyclosporin determination are collected in two EDTA coated polystyrene tubes (1 ml each) at each time point and are deep frozen at −20° C. after gentle agitation. Cyclosporin is assayed in whole blood using RIA with specific and/or non-specific MAB assay—detection limit in both cases=ca. 10 ng/ml.

In trials carried out in accordance with the above protocoll, e.g. comparing the composition of example 6 in hard gelatin encapsulated form with the current Ciclosporin drink solution (Ciclosporin=50 mg, LABRAFIL=150 mg, ethanol=50 mg, maize oil=213 mg, in soft gelatin encapsulated form : content end weight=463 mg/dosage) as standard, substantially increased bioavailability levels for the example 6 composition are recorded in comparison with the standard as reflected in both AUC (0–32 hrs) and Cmax values established. In addition, comparison of variation in whole blood Ciclosporin concentration (as determined by specific monoclonal RIA) with time following single administration of test compositions to a Ciclosporin dosage of 150 mg, demonstrates marked reduction in variability of response between all subjects receiving composition in accordance with example 1 as compared with that for all subjects receiving the standard composition.

Similar or equivalent results may be obtained following oral administration of other compositions in accordance with the invention, e.g. as herein described in examples 1 through 5 or 7.

I claim:

1. A pharmaceutical composition for oral administration comprising cyclosporin A as active ingredient in a carrier medium comprising a mixture of monoglyerides, diglycerides and triglycerides and a reaction product of a natural or hydrogenated castor oil and ethylene oxide.

2. The composition of claim 1, wherein the amount of cyclosporin A is about 2.0 to about 20% by weight, based on the total weight of said composition.

3. The composition of claim 1, wherein said amount of monoglyceride is about 25 to about 50% by weight, based on the total weight of said monoglycerides, diglyerides and triglycerides.

4. The composition of claim 1, wherein said carrier medium further comprises ethanol.

5. The composition of claim 1, wherein said carrier medium further comprises a transesterification product of a natural vegetable oil triglyceride and a polyalkylene polyol.

6. The composition of claim 1, wherein said reaction product is a reaction product of a natural castor oil and ethylene oxide.

7. The composition of claim 1, wherein said reaction product is a reaction product of a hydrogenated castor oil and ethylene oxide.

8. A pharmaceutical composition for oral administration comprising cyclosporin A as active ingredient in a carrier medium comprising a mixture of monoglycerides, diglycerides and triglycerides, a reaction product of a natural or hydrogenated castor oil and ethylene oxide and a transesterification product of a natural vegetable oil triglyceride and a polyalkylene polyol.

9. The composition of claims 8, wherein the amount of cyclosporin A is about 2.0 to about 20% by weight, based on the total weight of said composition.

10. The composition of claim 8, wherein the amount of monoglyceride is about 25 to about 50% by weight, based on the total weight of said monoglycerides, diglycerides and triglycerides.

11. The composition of claim 8, wherein said reaction product is a reaction product of a natural castor oil and ethylene oxide.

12. The composition of claim 8, wherein said reaction product is a reaction product of a hydrogenated castor oil and ethylene oxide.

* * * * *